United States Patent [19]

Gebeyehu et al.

[11] Patent Number: 4,921,805
[45] Date of Patent: May 1, 1990

[54] NUCLEIC ACID CAPTURE METHOD

[75] Inventors: Gulilat Gebeyehu, Silver Spring; Leonard Klevan, Derwood; John D. Harding, Potomac, all of Md.

[73] Assignee: Life Technologies, Inc., Gaithersburg, Md.

[21] Appl. No.: 414,728

[22] Filed: Sep. 29, 1989

Related U.S. Application Data

[63] Continuation of Ser. No. 78,991, Jul. 29, 1987, abandoned.

[51] Int. Cl.$^5$ ............................................. C12N 1/08
[52] U.S. Cl. ........................................ 435/270; 435/6; 436/178; 436/501; 436/526; 935/19; 935/85
[58] Field of Search ............... 436/94, 178, 501, 526; 435/6, 270, 803; 935/19, 85; 210/635, 656

[56] References Cited

U.S. PATENT DOCUMENTS

| | | | |
|---|---|---|---|
| 4,119,521 | 10/1978 | Chirikjian | 204/299 R |
| 4,563,417 | 1/1986 | Albarella et al. | 436/504 |
| 4,599,303 | 7/1986 | Yabusaki et al. | 435/6 |
| 4,665,184 | 12/1987 | Dervan et al. | 546/109 |

OTHER PUBLICATIONS

Sharp, P. A. et al., Biochemistry 12: 3055–3063 (1973).
Dervan et al., J. Amer. Chem. Soc., 100: 1968–1970 (1978).
Vacek, A. T. et al., Anal. Biochem., 124: 414–420 (1982).
Thomas, K. A. et al., Anal. Biochem., 91: 209–223 (1978).
Dervan and Becker, J. Amer. Chem. Soc., 100:6 (1978).
Kimberly and Goldstein, Anal. Chem., 53:789 (1981).
Barry et al., J. Chem. Soc. (Dalton Trans.), p. 2086 (1974).

*Primary Examiner*—Christine M. Nucker
*Assistant Examiner*—Lyle Alfandary-Alexander
*Attorney, Agent, or Firm*—Saidman, Sterne, Kessler & Goldstein

[57] ABSTRACT

A nucleic acid capture reagent which comprises one or more molecules that are capable of intercalation into nucleic acids and are attached to a solid support via a molecular linker. This capture reagent is useful for the separation and isolation of nucleic acids from complex unpurified biological solutions such as serum, sputum, blood, and urine. The resulting capture reagent-nucleic acid complexes are easily isolated from the sample solution by mechanical or magnetic means and the bound nucleic acids are released by simple chemical treatment.

10 Claims, No Drawings

NUCLEIC ACID CAPTURE METHOD

This application is a continuation, of application Serial No. 07/078,991, filed July 29, 1987 now abandoned.

BACKGROUND OF THE INVENTION

1. Field of the Invention

The present invention relates to the field of separation and isolation or purification of nucleic acids from complex biological or clinical specimens.

2. Brief Description of the Background Art

Various methods of separating deoxyribonucleic acids (DNA) from liquid biological samples are known in the art, but are very time consuming or otherwise plagued by complication.

It is known that DNA adheres to nitrocellulose. The liquid sample containing DNA is applied to a nitrocellulose filter and the DNA adheres or binds to the filter. The problem encountered is that proteins also bind to the nitrocellulose. Therefore this method is not specific for DNA alone.

Another method of separating DNA from samples is ultracentrifugation with sucrose or cesium chloride density gradients. The DNA is separated from other macromolecules such as proteins by this method according to its buoyant density or sedimentation coefficient. The biological sample is layered onto the density gradient in a centrifuge tube and is spun at very high speeds for long periods of time for the DNA to travel through the density gradient. This method, although satisfactory, is very time consuming and labor intensive. The centrifugation time may be 20 hours or more per sample. Furthermore, if the sample is spun too long, the DNA will separate from the sample but will pass entirely through the gradient to the very bottom of the centrifuge tube along with other constituents in the sample. Therefore, this method is also not suitable as a fast and easy method for separating DNA from complex samples.

Chemical methods of separating DNA from liquid samples are also known. Phenol extraction and ethanol precipitation are standard laboratory procedures, but each has its difficulties. Phenol is a toxic substance, and phenol extraction requires subsequent time-consuming procedures such as extraction with other organic reagents or dialysis to purify the sample. Furthermore, the separation of DNA from complex mixtures is subject to interference from molecules with nucleic acid binding properties. Ethanol causes many proteins, not just DNA, to precipitate, so the DNA must then still be separated from all other proteins in the sample.

Finally, agarose or polyacrylamide gel electrophoresis is used to separate DNA from biological samples. In this method the sample is applied to one end of a glass or plastic receptacle containing the gel and an electric current is applied across the length of the receptacle. The negatively charged nucleic acid molecules move toward the anode, the larger molecules moving more slowly. The rates of migration of the molecules depend on their molecular weights and on the concentration and degree of cross linking in the gel material. The DNA is then removed from the gel by cutting out that portion of the gel in which the DNA is located and finally extracting the DNA. Again, this method is time consuming and labor intensive, and the DNA must still be separated from the gel.

When DNA is separated by the electrophoresis gel method, it is necessary for the DNA to be stained in some manner to be visualized. Typically, ethidium bromide (EtBr) is used as the staining agent. Ethidium bromide adheres to the DNA by intercalation between the base pairs of the double helix structure of the DNA. The use of ethidium bromide in staining DNA is described in Sharp, P.A., et al. "Detection of Two Restriction Endonuclease Activities in *Haemophilus Parainfluenzae* Using Analytical Agarose-Ethidium Bromide Electrophoresis," *Biochemistry* 12:3055–3063 (1973). This reference discloses a rapid assay for restriction enzymes in which ethidium bromide is used to stain the DNA.

In a somewhat different application of ethidium bromide as a staining agent, ethidium bromide has been linked to a solid support. U.S. Pat. No. 4,119,521, issued to Chirikjian on Oct. 10, 1978, discloses a fluorescent DNA intercalating agent derivative of activated polysaccharides. The derivatives in the patent function as fluorescent stains to provide direct visualization of the DNA and their fractions, under the excitation of shortwave, ultraviolet radiation. The intercalating agents used in the patent are ethidium halides with the preferred agent being ethidium bromide. This agent is coupled covalently to an activated polysaccharide such as agarose.

Dervan P. B., and Becker, M. M., "Molecular Recognition of DNA by Small Molecules. Synthesis of Bis(-methidium)spermine, a DNA Polyintercalating Molecule," *J. Amer. Chemical Society* 100:1968–1970 (1978), discloses the synthesis and study of bis(methidium)spermine (BMSp). This molecule was described as a polyintercalator due to the presence of two separate methidium intercalating agents connected by means of the spermine linker. Spermine was chosen to link the intercalators because of its known affinity for nucleic acid and its length, which allows a geometry sufficient to reach nonadjacent intercalation sites in accordance with the neighbour exclusion binding model.

The studies of Dervan and Becker further showed that BMSp and ethidium bromide intercalated in similar manners. However, the BMSp has a binding constant several orders of magnitude stronger than the monomer, ethidium bromide.

Vachek, A. T. et al., *Analytical Biochemistry* 124:4–420 (1982), discloses an ethidium-acrylamide affinity medium for recovering nucleic acids from free solution and from polyacrylamide and agarose gels. This affinity medium is composed of an acrylamide matrix to which ethidium bromide is attached. Apparently, the nucleic acids can be eluted from this medium with a buffered salt solution and directly concentrated by ethanol precipitation.

The ethidium-acrylamide affinity medium is synthesized by the reaction, in the presence of a polyacrylamide matrix, of ethidium bromide, BIS (N,N'-methylenebisacrylamide), TEMED(N,N,N',N'-tetramethylethylenediamine), and ammonium persulfate in a suitable buffer. When ethidium bromide is present, it presumably becomes covalently linked to the acrylamide matrix through methylenebisacrylamide spacer arms.

This reference discloses the use of Bio-Gel P-4 as the particulate acrylamide matrix. The cross-linking properties of methylenebisacrylamide are evidently important for the linking of ethidium to Bio-Gel P-4. The binding of ethidium to this gel is also somewhat dependent on the composition of the buffer in the reaction. The authors noted that allowing ample time for interaction with the affinity medium (i.e., flow rates of 0.44 ml/min for a 3-ml bed volume in a 6-ml syringe and a 15-min equilibration) was essential for quantitative binding. However, elution of the RNA shortly after 15-min equilibration with the column was necessary to avoid some apparently irreversible binding.

Thomas, K. A. and A. N. Schechter, *Analytical Biochemistry*, 91:209-223 (1978) discloses direct physical measurements on substituted agarose gels and evidence of intercalation of gel-bound ethidium into transfer-RNA. This reference reports that the cation of the salt ethidium bromide (3,8- diamino-5-ethyl-6-phenyl-phenanthridinium bromide) has been covalently linked to an agarose matrix through an intermediate 3,3'-diaminodipropylaminosuccinyl spacer arm.

The paper also discloses the stoichiometry and nature of the binding of tRNA to ethidium cations that have been covalently bound to an agarose gel as determined from partition binding and direct spectral measurements of the gel itself. Various measurements were made to study the ethidium-tRNA interaction. Fluorescence enhancement and spectral red shift were observed and determined to be proportional to the amount of tRNA bound to the gel. Experiments also showed that increasing the NaCl concentration decreased the percentage of tRNA bound to the gel. A molar concentration of approximately 1.3 or higher resulted in 0% binding. The authors concluded that the ethidium bromide bound to the tRNA by intercalation. This reference does not document any actual or speculative use of the capture reagent for isolating DNA or RNA from complex unpurified mixtures such as clinical samples. Therefore, a need continues to exist for a rapid and efficient method of separating DNA from unpurified clinical samples.

SUMMARY OF THE INVENTION

The nucleic acid capture reagent of the invention comprises a molecule capable of intercalation into a DNA helix. The intercalator is attached to a solid support via a molecular linker. The intercalating molecule, and in some cases the linker, bind to nucleic acids present in a buffer system or a complex biological fluid. The inert properties of the solid support allow separation of the resulting capture reagent-nucleic acid complexes from non-binding material by means of simple procedures such as a short centrifugation or filtration. Once the capture reagentnucleic acid complex has been separated from the remainder of the sample, the bound nucleic acid can be released and separated from the capture reagent in a simple manner. The released nucleic acid can be characterized and quantitated by procedures such as molecular hybridization.

The capture reagent of the invention may be used to isolate nucleic acids from unpurified biological samples, e.g., serum, cervical samples, stool samples, sputum, blood, urine, body tissues and body fluids. The capture reagent may also be used to separate hybridized nucleic acids from small nucleic acid fragments resulting from enzymatic digestion of unhybridized material. Furthermore, the capture reagent may be used to separate supercoiled plasmids from linear DNA and nicked circular DNA in plasmid preparations. Also, the capture reagent of the invention may be used to isolate nucleic acids from solubilized agarose or acrylamide gels. Other samples that contain or comprise DNA may be used with the capture reagent and methods of this invention.

These samples may be tested by routine screening using the capture reagent and the methods of this invention to ascertain the efficacy of the invention for any particular DNA and sample.

The removal of the capture reagent from the complex biological solution may be accomplished by centrifugation, filtration, or in the case where magnetic cellulose is used as the solid support, by the use of a magnetic field.

DESCRIPTION OF THE PREFERRED EMBODIMENTS

The nucleic acid capture reagent of the invention comprises an intercalating moiety capable of intercalating into double stranded nucleic acid molecules, connected by means of a linker molecule to a solid support.

Specifically, the intercalating moiety may be ethidium or methidium or any other intercalating molecule such as actinomycin, malachite green, phenyl neutral red, or derivatives of acridine. The linker molecule may be charged or uncharged and may be of the form

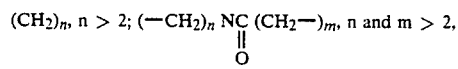

or other methylene groups joined together with more than 2 amide bonds:

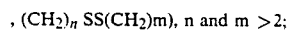

and polyamines such as spermidine and spermine, which are positively charged at their internal secondary amines near neutral ph. The linker is most preferably spermine.

The solid support may be a beaded material such as sepharose, agarose or magnetic cellulose, or may be a plastic material in the form of a tube, dipstick, or microtiter plate, or may be in the form of a membrane such as nylon.

The intercalating moiety and the solid support are first modified in such a way that they can be joined together through an amide, carbamate, urea, ether, thioether, amine or other linkage commonly used for immobilization (*Affinity Chromatography*. Hoffman-Osterhof, ed.; Pergamon Press, 1978; *Affinity Chromatography*, publication of Pharmacia Fine Chemicals). For example, if the solid support is modified to contain a carboxy group, then the intercalator may be modified to contain a reactive amine through addition of a linker such as spermine or diaminoalkane. Using coupling agents such as dicyclohexylcarbodiimide, the support and the intercalator can be joined together through an amide bond. Alternatively, the carboxyl group can be converted to a reactive ester (such as N-hydroxysuccinimide ester) which will then react with the amine. Conversely, the support can be modified with an amine and the intercalator can be modified to contain a carboxyl group and the two moieties coupled together as described above.

It is not necessary to pre-purify the clinical biological samples which may contain nucleic acids. The capture reagent of the invention is suspended in deionized water, is added to the biological sample, and is incubated for a time sufficient to allow binding of the capture reagent to the nucleic acids to form capture reagent-nucleic acid complexes. The incubation time is usually 30 minutes at room temperature. The capture reagentnucleic acid complexes are isolated from the sample by centrifugation, filtration, or by magnetic separation.

Finally, the nucleic acids are separated from the isolated complexes by, for example, treating the capture reagent-nucleic acid complexes with dilute alkali. For example, the complexes may be mixed with NaOH and centrifuged. The supernatant will contain the nucleic acids now separated from the capture reagent. It is to be noted that crude samples such as human serum may be used in large quantities, e.g., 2 ml.

A. Synthesis Of The Capture Reagent

The nucleic acid capture reagent containing methidium linked to sepharose or magnetic cellulose via a spermine linker was synthesized as follows. P-carboxylmethidium chloride was synthesized from o-aminobiphenyl by the procedure of Dervan and Becker (*J. Amer. Chem. Soc.* 100(6):1968 (1978)), which is incorporated herein by reference. Spermine was linked to the p-carboxylmethidium chloride by first activating the carboxyl group with carbonyldiimidazole and treating the imidazolidate thus formed with excess spermine. The methidium spermine adduct was purified by flash chromatography and immobilized onto an inert support by reaction with N-hydroxysuccinimide activated sepharose or periodate activated magnetic cellulose. Alternatively, a magnetic cellulose containing reactive amines was treated with disuccinimidyl substrate followed by methidium-spermine to give the DNA capture reagent.

B. Uses Of The Reagent

Experiments were performed in which radioactively labeled DNA was added to a buffer or biological fluid, the solution was incubated with capture reagent and the resulting DNA-capture reagent complex was separated from the sample by centrifugation. DNA was released from the capture reagent by treatment with dilute NaOH and quantitated. These experiments indicated that greater than 80% of the radioactive DNA initially present in the solution was bound by the reagent and that greater than 95% of the bound DNA was released by treatment with sodium hydroxide. Buffers that were tested included: (1) Tris-HCl buffer containing EDTA and various concentrations of NaCl (0.1 to 3 M), (2) Tris-HCl buffer containing protein denaturants such as urea and guanidine hydrochloride, and (3) cell transport medium containing 0.5% Triton X-100 and buffers.

These experiments also indicated quantitative binding of small amounts (e.g. nanograms) of DNA present in relatively large volumes (e.g. 0.5-1.0ml) of sample and large amounts of DNA (e.g. micrograms) present in small volumes (less than 100ul) of sample.

Experiments were performed which indicated that the capture reagent can be used to isolate specific DNA sequences of clinical interest from biological fluids, that the DNA released from the reagent by incubation in dilute NaOH solution can be bound to a solid support (nitrocellulose or nylon membranes) and identified and quantitated by means of molecular hybridization protocols. Specifically, picogram quantities of human papilloma virus DNA were isolated from solutions in which material present in cervical swabs was suspended and-/or dissolved. The percentage of viral DNA captured by the reagent was then quantitated by hybridization. Likewise, picogram quantities of Hepatitis B virus DNA were isolated from human serum using the capture reagent of the invention and quantitated by hybridization.

Having now generally described the invention, the same will be understood by means of specific examples which are, however, not intended to be limiting unless otherwise specified.

EXAMPLES

A. ISOLATION OF NUCLEIC ACIDS FROM AQUEOUS SOLUTIONS BASIC PROTOCOL
(varied as described in examples below).

A nucleic acid solution (usually in a volume of 30-100 microliters) is aliquoted into a plastic microcentrifuge tube. A suspension of the capture reagent is prepared in a separate tube. (This suspension is prepared by first pelleting the capture reagent by centrifugation for 3 min. in a clinical centrifuge. Three volumes of deionized water are added to the pellet. The water and capture reagent are mixed by vigorous vortexing for a few seconds until the reagent is uniformly suspended). The suspended capture reagent (usually a volume of 50-100 microliters) is added to the DNA sample, the tube is vortexed and immediately placed on a rotator for 30 min. at room temperature. The tube is removed from the rotator and centrifuged for 3 min. at room temperature in a microcentrifuge or clinical centrifuge at top speed. The pellet obtained from this centrifugation contains the capture reagent and any nucleic acid bound to it, i.e., the capture reagent-nucleic acid complex. The pellet is washed with 300 microliters TE buffer and centrifuged as before. 0.5 M NaOH (usually a volume of 500 microliters) is added to the capture reagent pellet. The tube is vortexed vigorously to mix the capture reagent and the NaOH and the tube is immediately placed on a rotator for 10 min. at room temperature. The tube is centrifuged as above. The supernatant (which contains nucleic acid released from the reagent) is characterized either by liquid scintillation counting (if the nucleic acid is radioactive) or by blotting protocols involving binding of the nucleic acid to a solid support followed by hybridization with a suitable detection probe.

EXAMPLE 1

The nucleic acid sample contained 11 ng of radioactive DNA in 30 microliters of TE buffer (TE buffer is 10 mM Tris-HCl, pH 7.5, 1 mM EDTA). The radioactive DNA was the "1 Kb Ladder" sold by Bethesda Research Laboratories, which is comprised of fragments of a yeast DNA sequence which vary in size in increments of 1 kilobase, labelled with $^{32}P$. In various experiments, 77-95% of the labelled DNA was bound by the reagent. These same high levels of capture were obtained in TE buffer containing 3 M, 0.1 M or no additional NaCl, and in TE buffer containing as much as 500 mM EDTA. In these experiments, 77-100% of the bound DNA was released by treatment with 0.5 M NaOH as described above. These experiments demonstrate that DNA can be captured from buffers commonly used in studies of nucleic acids and that capture is independent of salt concentration.

EXAMPLE 2

Experiments similar to those of Example 1 were performed using phage lambda DNA labelled with $^{32}P$ by nick translation. Similar results were obtained. Thus, capture is independent of the DNA sequence used in the experiment. (Capture of Hepatitis and Papilloma virus sequences is described in Examples 9-12 below.)

EXAMPLE 3

Experiments similar to those of Example 1 were performed in which the amounts and volumes of DNA solutions were varied. These experiments indicated that relatively small amounts of DNA can be captured from relatively large volumes (e.g., 95% capture of 10 ng of DNA from 0.5 ml of TE buffer), and that relatively large amounts of DNA can be captured from relatively small volumes (e.g., 95% capture of 1 ug of DNA from 30 microliters of TE buffer). In all cases, greater than 80% of the captured DNA was released by treatment with 0.5 M NaOH. The capture, release and detection of pg quantities of viral DNAs is demonstrated in Examples 9-12 below.

EXAMPLE 4

Experiments similar to those of Example 1 were performed in which the DNA was present in an aqueous solution containing a protein denaturant. In all cases, greater than 80% capture and greater than 80% release of captured DNA were obtained. The solutions tested contained: 8 M urea, 5% sodium dodecyl sulphate, or 6 M guanidine hydrochloride.

EXAMPLE 5

Experiments similar to those of Example 1 were performed in which radioactive RNA was used. Greater than 90% of the RNA was captured and greater than 90% of the radioactivity was released by treatment with NaOH. The RNA was a copy of the Papilloma virus 18 genome prepared by copying a cloned Papilloma virus DNA sequence using phage T7 RNA polymerase. This experiment demonstrates that the capture reagent binds RNA.

EXAMPLE 6

Using a protocol similar to that of Experiment 1, Hind III fragments of phage lambda DNA, terminally labelled with $^{32}P$, were captured and released with NaOH. The DNA was electrophoresed on an alkaline agarose gel and the gel was autoradiographed. Undegraded DNA molecules of the correct expected sizes were present in a DNA sample captured from TE buffer and in a DNA sample captured from human serum. Undegraded DNA molecules were also obtained when the "1 KB ladder" (consisting of yeast DNA fragments, sold by Bethesda Research Labs) was used in the experiment. Thus, DNA molecules ranging in size from as little as c. 300 bp to greater than 10,000 bp can be isolated in intact form using the capture reagent.

B. ISOLATION OF DNA FROM HUMAN SERUM.

EXAMPLE 7

50 microliters of serum from healthy human males (purchased from Sigma Chemical Co.) were treated to disrupt virus particles and liberate viral DNA, and 1 microliter of $^{32}P$ labelled phage lambda DNA (10 ng) was added. This sample was incubated at 65 degrees C. for 1 hr. (This treatment is commonly used to disrupt and deproteinize virus particles.) Fifty microliters of suspended capture reagent was added to the serum sample and placed on a rotator for 30 min. at room temperature. The capture reagent (and bound DNA) was isolated by centrifugation as in Example 1, the bound DNA was released by treatment with 0.5 N NaOH and counted in a liquid scintillation counter. In a typical experiment 80% of the labelled DNA was bound by the capture reagent and 95% of the bound DNA was released. This experiment indicated that DNA can be isolated from serum. The experiment described in Example 6, above, indicates that DNA isolated from serum is undegraded after capture.

EXAMPLE 8

An experiment similar to that of Example 7 was performed in which 2 ml of serum was used (this is a volume of serum which cannot normally be analyzed by a procedure as simple as that described here using a capture reagent). Incubation was with 500 microliters of capture reagent for 15 hours at room temperature. In typical experiments in which either 140 ng or 100 pg, respectively, of labelled phage lambda DNA were used, greater than 90% of the DNA was bound by the reagent and 95% of the bound DNA was released by NaOH treatment. This experiment demonstrates that DNA can be captured efficiently from relatively large (milliliter) volumes of serum, thus extending possible diagnostic uses of the reagent to situations in which virus or DNA concentrations in serum are very low.

EXAMPLE 9

To determine whether non-radioactive DNA could be isolated from serum and quantitated by blotting protocols, the following experiment was performed. An experiment similar to that of Example 7 was performed in which 50 microliter aliquots of serum from healthy males were "spiked" with amounts of unlabelled DNA ranging from 0 to 100 pg. The DNA was cloned plasmid DNA containing a copy of the Hepatitis B virus genome. The DNA was captured and released as in Example 7. The samples were applied to a nylon membrane (Biodyne, Pall Corp.) using a "dot blot" apparatus (Bethesda Research Labs) attached to a vacuum pump. Also applied in a similar manner were 500 microliter aliquots of the plasmid DNA in 0.5 N NaOH as positive controls and concentration standards. Negative controls, consisting of 0.5 N NaOH only, were also applied. The nylon filter was hybridized with radioactive RNA homologous to the Hepatitis B virus DNA, washed and autoradiographed by standard protocols. Inspection of autoradiographs indicated that 0.5 pg of DNA spiked into serum could be detected. Samples obtained from serum samples that had no spiked DNA gave no signal on the autoradiograph. Comparison of the intensities of autoradiographic signals obtained from captured DNA samples and signals obtained from the uncaptured, positive control samples indicates that the efficiency of detection is c. 50%. This experiment indicated that the capture reagent can be used to isolate and detect viral DNA sequences present in serum with very low levels of non-specific, background signals.

EXAMPLE 10

The following experiment was performed to determine whether DNA present in virus particles can be isolated from serum and quantitated. We obtained a serum sample from a patient who had clinical symptoms of hepatitis, whose blood tested positive for the Hepatitis B virus, HBe and HBs antigens, and whose serum had been previously determined to contain more than 500 pg of Hepatitis B virus DNA per 50 microliters. A set of serial dilutions of this serum were made into normal (uninfected) serum and 50 microliter aliquots were treated with capture reagent as in Example 7. DNA released by the capture reagent was bound to a nylon filter and quantitated by hybridization as in Example 9. The results of this experiment indicate that the patient's serum contained c. 600 pg of Hepatitis B virus DNA per 50 microliters and that the DNA in a 1/1200 dilution (containing c. 0.5 pg viral DNA) could be detected unambiguously over background.

EXAMPLE 11

A panel of 17 serum samples from patients displaying clinical symptoms of hepatitis (but not necessarily type B hepatitis) was tested as in Example 10. Hepatitis B virus DNA was detected in all samples that contained both Hepatitis B virus HBe and HBs antigens. The assay using the capture reagent indicated that individual samples contained from 5 to 500 pg of viral DNA per 50 microliters of serum. Hepatitis B virus DNA was not detected in serum samples that did not contain Hepatitis B virus HBe and HBs antigens. This experiment (along with that of Example 10) indicates that the capture reagent can be used in diagnostic tests to detect the presence of viral DNA in human serum with high sensitivity.

C. ISOLATION OF DNA FROM HUMAN CERVICAL SAMPLES.

EXAMPLE 12

Swabs containing cervical epithelial cells obtained from women who tested negative for the presence of Papilloma virus were incubated in a reagent solution to disrupt any virus particles in the cervical sample. Approximately 200 microliters of the solution was obtained after the swab was removed from the solution. This solution was divided into two 100 microliter aliquots. To one of the aliquots was added a given amount of a plasmid containing a cloned Papilloma virus 18 sequence; no additional DNA was added to the second aliquot. The amounts of DNA added to the first aliquot of the cervical sample were 100, 10, or 1 pg of plasmid DNA, respectively. Triplicate samples of each DNA concentration were prepared. Thus, there were 18 samples in all (9 swabs, each divided into 2 aliquots, one aliquot of which contained no added DNA). To each of the 18 samples was added 30 microliters of suspended capture reagent and the nucleic acid was captured and released with 0.5 N NaOH essentially as described in Example 1. The released DNA samples were immobilized on a nylon membrane by dot blotting as in Example 9. Also applied to the filter in a similar manner were 500 microliter aliquots of Papilloma virus DNA-containing plasmid DNA in 0.5 M NaOH as positive controls and concentration standards for detection as well as aliquots of 0.5 M NaOH which contained no DNA (as negative controls).

The filter was hybridized with radioactive Papilloma virus RNA (obtained by copying a cloned plasmid DNA that contains a copy of the Papilloma virus genome with T7 phage RNA polymerase). Hybridization and post-hybridization washes of the filter were performed using standard procedures for detection of Papilloma virus DNA on nylon filters. The filter was autoradiographed. The autoradiograph revealed that the aliquots of papilloma DNA "spiked" into the cervical samples could be detected following a 42 hr. exposure of the autoradiograph. Furthermore, the aliquot of each cervical sample to which no Papilloma DNA had been added gave no signal on the autoradiograph, indicating that non-specific signals were not obtained in samples treated with the capture reagent. The autoradiographic signals obtained from the cervical samples and those from the positive control standards were scanned using a laser densitometer (LKB Instruments, Inc.) and compared to measure the efficiency of detection of the captured DNA. For the 10 pg spots, this value was 25–31%. This experiment indicates that the capture reagent can be used to isolate and quantitate Papilloma virus sequences present in human cervical samples with very low non-specific backgrounds. Thus, the capture reagent can be used in clinical tests to detect viral nucleic acids present in cervical samples.

D. ISOLATION OF DNA FROM HUMAN URINE.

EXAMPLE 13

Urine was obtained from a healthy male. One-hundred picograms of radioactive phage lambda DNA was added to a 50 microliter or 500 microliter aliquot of urine. The urine was incubated as in Example 7 for 1 hr. at 65 degrees C. One-hundred microliters of suspended capture reagent was added to each aliquot, the DNA was captured for 15 hours and released as in Example 1. The overall yield of released DNA relative to the DNA originally "spiked" into the urine was 54% for 50 microliter aliquots of urine and 55% for 500 microliters of urine, respectively. Thus, the capture reagent can be used to isolate DNA from urine.

E. COMPARISON OF THE METHIDIUM-SPERMINE CAPTURE REAGENT OF THE INVENTION AND ACRYLAMIDE-ETHIDIUM REAGENT.

Two preparations of the Acrylamide-Ethidium reagent described by A. Vacek et al., *Analytical Biochemistry* 124:414–420 (1982) were synthesized. Their ability to capture DNA was compared with that of two preparations of the Methidium-Spermine-Sepharose capture reagent as taught by the invention.

The Acrylamide-Ethidium reagent had a very low affinity for DNA present in human serum, human serum treated with protein denaturants and human urine, respectively. In contrast, the Methidium-Spermine reagent captured 90% of the DNA present in these solutions. Thus, the reagent of the invention can be used for clinical applications which preclude the use of the Acrylamide-Ethidium reagent.

The relative abilities of the two types of reagents to bind DNA in buffers of different ionic strengths were also examined. The Methidium-Spermine reagent of the invention bound greater than 80% of DNA at salt concentrations as high as 3 Molar NaCl. In contrast, the Acrylamide-Ethidium reagent had a markedly reduced capacity to bind DNA at NaCl concentrations of 1 M or greater. This characteristic of the Acrylamide-Ethidium reagent makes it much less useful than the reagent as taught by the invention for analysis of samples which can potentially vary in ionic strength or which contain greater than 1 M salt.

A. EXPERIMENTAL DETAILS

1. Test Preparations.

Two preparations of the Methidium-Spermine-Sepharose reagent (preparations #4 and #5) were synthesized as described in the Description of the Preferred Embodiments—A. Synthesis of the Capture Reagent.

Two preparations of Acrylamide-Ethidium reagent were prepared exactly as described by Vacek et al. (preparations #1 and #2).

All four reagent preparations were suspended in distilled water such that a given volume of suspended reagent contained an equal weight of reagent for each preparation.

2. Sample Reactions.

Reactions were set up as follows: The sample was in a volume of 100 microliters. Samples were: (a) Human serum treated with protein denaturants (standard protocol for detection of Hepatitis virus DNA); (b) Untreated human serum: To 50 microliters of human serum was added 50 microliters of TE buffer (10 mM Tris HCl, 1 mM EDTA, pH 7.5); and (c) Human urine: 100 microliters of urine from a healthy male was used.

To each of these solutions (total volume 100 microliters) was added 8 ng of $^{32}$P-labelled DNA (BRL, 1 KB ladder) in 5 microliters of TE buffer. Fifty microliters of suspended capture reagent was added and the tube was placed on a rotator for 30 min. at room temperature. The tube was spun in a microcentrifuge for 3 min., the supernatant was removed with a micropipet and released into a solution of 5% trichloroacetic acid (to precipitate any uncaptured radioactive DNA). The capture reagent pellet was washed with 300 microliters of TE buffer, spun as before and the supernatant added to the 5% TCA solution. The TCA solutions were filtered through glass-fiber discs which were counted in a liquid scintillation counter. The amount of DNA that had not been captured was determined, and by difference, the amount of captured DNA was calculated. All samples were tested in triplicate.

For experiments to examine the effects of salt concentration on capture, 100 microliter samples of TE buffer containing 8 ng of $^{32}$P labelled DNA and a given molarity of NaCl were incubated with 50 microliters of suspended capture reagent and further analyzed as described for the serum samples, above.

B. RESULTS.

The results of the serum and urine capture experiments are shown in Table I, Part A, below. Both preparations of the Methidium-Spermine reagent of the invention captured >90% of the DNA present in treated serum, untreated serum, or urine. In contrast, neither preparation of the Acrylamide-Ethidium reagent captured any detectable amount of DNA from urine, and only a small amount of DNA was captured from urine. Thus, there are components in these samples which inhibit capture. The chemistry of this inhibition has not been further analyzed. Furthermore, it is noted that serum appears to release most of the bound Ethidium from the Acrylamide-Ethidium reagent, demonstrating that the Ethidium does not remain stably bound to the acrylamide matrix in these solutions. In contrast, the Methidium in the Methidium-Spermine reagent of the invention remained stably bound to the Sepharose matrix in these experiments.

The results of the capture experiments carried out in different concentrations of NaCl are summarized in Table I, Part B. Binding of DNA by the reagent of the invention is relatively insensitive to salt concentrations between 0 and 3 M NaCl. In contrast, binding of DNA by the Acrylamide-Ethidium reagent is reduced at 1 M NaCl, and binding capacity in 3 M NaCl is as low as 12% of its value in the absence of NaCl for one of the reagent preparations.

TABLE 1

COMPARISON OF METHIDIUM-SPERMINE AND ACRYLAMIDE-ETHIDIUM NUCLEIC ACID CAPTURE REAGENTS

A. Effects of Serum on Capture of DNA

| | Serum Treated | Serum Untreated | Urine |
|---|---|---|---|
| | (% DNA Captured)* | | |
| Methidium-Spermine Prep #4 | 96 | 95 | ND |
| Methidium-Spermine Prep #5 | 96 | 93 | 92 |
| Acrylamide-Ethidium Prep #1 | 0 | 0 | 8 |
| Acrylamide-Ethidium Prep #2 | 0 | 0 | 8 |

B. Effect of NaCl Concentration on Capture of DNA

| | Molarity of NaCl | | | | |
|---|---|---|---|---|---|
| | 0 | 0.5 | 1.0 | 2.0 | 3.0 |
| | (% DNA Captured)* | | | | |
| Methidium-Spermine Prep #4 | 95 | 88 | 93 | 82 | 93 |
| Methidium-Spermine Prep #5 | 97 | 97 | 99 | 99 | 99 |
| Acrylamide-Ethidium Prep #1 | 98 | 93 | 59 | 49 | 39 |
| Acrylamide-Ethidium Prep #2 | 98 | 90 | 36 | 20 | 12 |

*Average of triplicate samples
ND = Not Determined

The invention is not limited to those modes of its application and embodiments that have been described above. It encompasses any modifications that allow the binding of the capture reagent of the invention with nucleic acids by means of intercalation. These equivalents are included within the field of protection defined by the claims.

What is claimed is:

1. A method of separating nucleic acids from an unpurified biological sample comprising:
    (a) contacting an unpurified biological sample with a capture reagent, wherein said capture reagent comprises:
        (i) a solid support;
        (ii) a linker molecule comprising spermine or spermidine bound to said solid support; and
        (iii) a methidium moiety, bound to said linker; wherein said methidium moiety is able to bind to the nucleic acids in said biological sample independent of the salt concentration of said sample; and wherein a sample-capture reagent mixture is formed thereby;
    (b) insulating said sample-capture reagent mixture for a time and under conditions sufficient to allow said capture reagent to bind to nucleic acids in said sample to form a capture reagent-nucleic acid complex; and
    (c) isolating said complex from said mixture.

2. The method of claim 1 wherein said isolating is performed by the method selected from the group consisting of centrifugation, filtration, and magnetic separation.

3. The method of claim 1 further comprising:
    (a) treating said isolated complex to effect release of said nucleic acid therefrom; and (b) separating said released nucleic acids from said isolated complex.

4. The method of claim 3 wherein step (a) comprises treating said capture reagent-nucleic acid complex with dilute alkali.

5. The method of claim 1 wherein said solid support is a beaded material.

6. The method of claim 5 wherein said beaded material is selected from the group consisting of sepharose, agarose, or magnetic beads.

7. The method of claim 1 wherein said solid support is a polymer.

8. The method of claim 7 wherein the form of said polymeric solid support is selected from the group consisting of a tube, a dipstick, or a microtiter plate.

9. The method of claim 1 wherein said solid support is a membrane.

10. The method of claim reagent of claim 9 wherein said membrane comprises nylon.

* * * * *